US00PP16072P2

(12) United States Plant Patent
Olesen et al.

(10) Patent No.: US PP16,072 P2
(45) Date of Patent: Oct. 25, 2005

(54) ***CLEMATIS* PLANT NAMED 'EVIPO011'**

(50) Latin Name: *Clematis viticella*
Varietal Denomination: Evipo011

(75) Inventors: Mogens N. Olesen, Fredensborg (DK); Raymond J. Evison, St. Sampsons (GB)

(73) Assignee: Poulsen Roser A/S, Fredensborg (DK)

( * ) Notice: Subject to any disclaimer, the term of this patent is extended or adjusted under 35 U.S.C. 154(b) by 78 days.

(21) Appl. No.: 10/927,711

(22) Filed: Aug. 27, 2004

(51) Int. Cl.[7] ..... A01H 5/00
(52) U.S. Cl. ..... Plt./228
(58) Field of Search ..... Plt./228

*Primary Examiner*—Kent Bell

(57) ABSTRACT

A new *Clematis* cultivar which is well suited to propagation in glasshouses, with a medium growth habit, profuse, light purple flowers with a distinct flower center, early flowering from previous season's growth and good disease resistance. The variety successfully propagates from softwood cuttings and is suitable for cultivation in commercial glasshouses. This new and distinct variety has shown to be uniform and stable in the resulting generations from asexual propagation.

2 Drawing Sheets

Botanical classification: Genus—*Clematis*. Species—*viticella*.
Variety denomination: 'Evipo011'.

SUMMARY OF THE DISCOVERY

The present discovery constitutes a new and distinct variety of *Clematis* which originated from a naturally occurring mutation of unknown causation on a branch of *Clematis* 'Evijohill', a *Clematis* by the same inventor, described and illustrated in U.S. Plant Pat. No. 12,912 dated Sep. 3, 2002.

'Evipo011' has a unique combination of characteristics which distinguish it from the *Clematis* 'Evijohill'. For example: 'Evipo011' has an inner 'ruff' at the flower center formed from petaloid stamens. 'Evijohill' has an inner 'ruff' at the flower center formed from relatively broad inner tepals.

The *Clematis* plant of the present discovery also has a unique combination of characteristics which distinguish it from all other varieties which we are aware of. For example, 'Evipo011':

1. has profuse light-purple flowers with a distinct center;
2. develops flowers in spring and autumn;
3. propagates and flowers more reliably than most double cultivars.
4. is well suited to container culture.

This combination of qualities was lacking in *Clematis* varieties that were in commercial cultivation and the qualities have been substantially achieved in the new variety.

'Evipo011' was discovered by Raymond J. Evison and Mogens N. Olesen in their *Clematis* development program in Domarie Vineries Les Sauvagees, St. Sampsons, Guernsey, Channel Islands, United Kingdom in May 2001.

Asexual reproduction of 'Evipo011' by cuttings was first done by Raymond J. Evison and Mogens N. Olesen in Domarie Vineries Les Sauvagees, St. Sampsons, Guernsey, Channel Islands, United Kingdom in June 2001. This initial and subsequent asexual propagations have demonstrated that the characteristics of 'Evipo011' are true to type and are transmitted from one generation to the next.

BRIEF DESCRIPTION OF THE DRAWING

The accompanying color illustration show as true as is reasonably possible to obtain in color photographs of this type:

FIG. 2.1 Upper and under surface of open flower;

FIG. 2.2 Stem showing attachment of petiole, leaves, pedicel, and closed flower buds;

FIG. 2.3 Flower buds at ¼ opening;

FIG. 2.4 Juvenile growth showing stem and attachment of leaves.

DETAILED DESCRIPTION OF THE VARIETY

Figure 1:
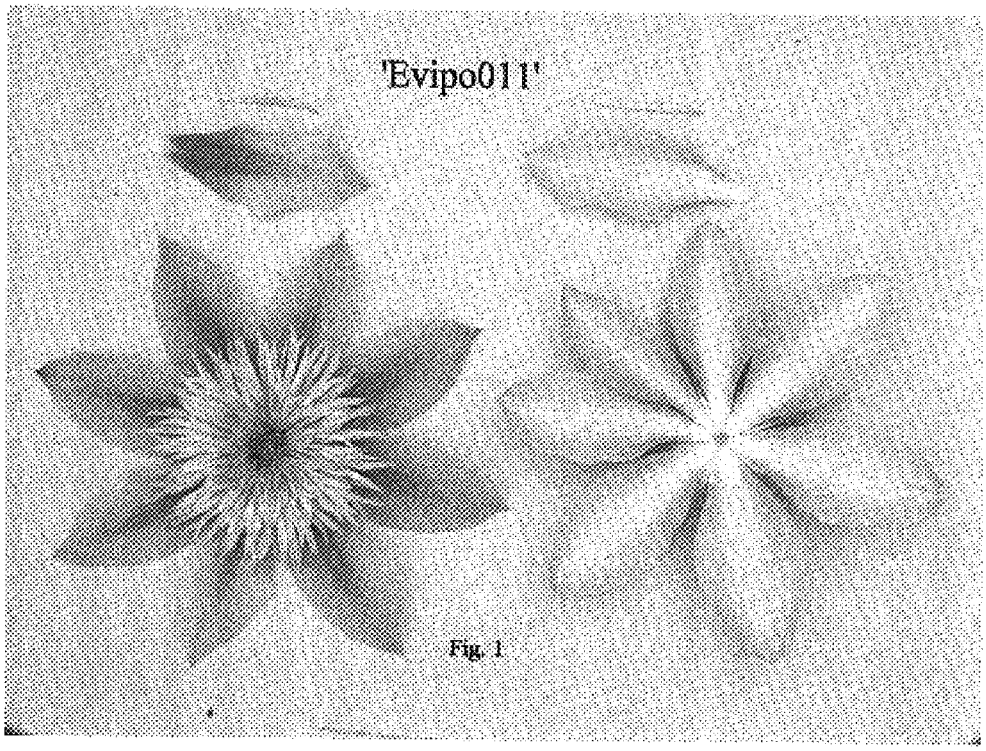
FIG. 1 Upper and lower side of open flower with detached tepals.

The following is a detailed description of 'Evipo011', as observed in its growth throughout the flowering period in glasshouses at Domarie Vineries Les Sauvagees, St. Sampsons, Guernsey, Channel Islands, United Kingdom. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001.

For a comparison, the nearest existing *Clematis* variety is 'Evijohill'. Chart 1 details the main distinguishing physical characteristic which differentiates 'Evipo011' from the comparison variety.

CHART 1

| | 'Evipo011' | 'Evijohill' |
|---|---|---|
| Flower center and reproductive organs | Center consists of an inner 'ruff' of 400 to 500 or more petaloid stamens, width 3 to 5 mm. | Center consists of many small tepals, quantity 50 to 100, width 5 to 10 mm. |

FLOWER AND FLOWER BUD

Blooming habit: Normal flowering period is April through May. Flowering is recurring August to October.

Flower bud:

*Size.*—35 mm length. Bud diameter is 18 mm.

*Bud form.*—Elliptic and somewhat pubescent.

*Bud color.*—Green Group 142B.

Peduncle:

*Aspects.*—Near horizontal and holds flower facing upwards.

*Surface.*—Pubescent.

*Length.*—60 to 100 mm average length.

*Color.*—Green Group 143C.

*Strength.*—Strong.

Receptacle: Absent.

Flower arrangement:

*Location on vine.*—New and old growth.

*Borne.*—Often borne singly in spring; otherwise, compound cyme cluster of 3 to 5 flowers.

Flower bloom:

*Size.*—110 to 130 mm in diameter. 30 to 40 mm in depth.

*Profile.*—Upon opening: Flowers are flat with protruding globular center. After opening: Flowers are flat with protruding globular center.

*Color.*—Upon opening: Upper surface is Purple Group 77C with a central bar of Red-Purple Group 70A. After opening: Upper surface is Purple Group 76C with a central bar of Red-Purple Group 72C. The reverse surface is Purple Group 76D.

*Variations.*—White Group N155A observed at tepal base.

*Fragrance.*—None.

*Lasting quality.*—On the plant: 15 to 20 days. As a cut flower: 7 to 10 days.

Tepals:

*Quantity.*—Normally 5 to 8.

*Size.*'Normally 55 to 65 mm in length by 25 to 35 mm wide.

*Shape.*—Individual tepal shape is ovate to elliptical.

*Margins.*—Entire.

*Undulation of margin.*—Slight.

*Tepal apex.*—Mucronate.

*Tepal base.*—Acute.

*Recurvature of tip.*—Weakly reflexed.

*Persistence.*—Tepals drop off cleanly leaving an inner 'ruff' of petaloid stamens.

*Arrangement.*—Tepals are arranged regularly.

Reproductive organs:

*Arrangement.*—Sterile.

Seed head characteristics: None.

PLANT

Plant form: Climbing.

Plant growth: Vigorous.

Size: Seasons growth attains 2.5 to 3 meters in height. Average spread is 1 to 1.5 meters.

Hardiness: Trials to date show the variety is cold tolerant to USDA hardiness zone 4.

Stems:

*Color.*—Young wood: Yellow-Green 143A quickly becoming Greyed-Orange Group 177A. Older wood: Greyed-Orange 172B.

*Internodes.*—Shape: Cylindrical. Length: 100 to 160 mm.

*Surface.*—Young wood: Smooth and somewhat pubescent. Older wood: Smooth.

Plant foliage:

*Leaf characteristics.*—Deciduous.

*Mature leaf form.*—Trifoliate. There are 3 leaflets on average.

*Compound leaf size.*—150 to 190 mm (l)×65 to 110 mm (w).

*Abundance.*—Generally, there are 16 leaves per 1000 mm of stem.

*Color.*—Upper surfaces of mature leaves: Green Group 137B. Lower surfaces of mature leaves: Green Group 137C. Upper surfaces of new foliage: Yellow-Green Group 143A. Lower surfaces of new foliage: Yellow-Green Group 143C.

Plant leaves and leaflets:

*Stipules.*—Absent.

*Petioles.*—Average length: 30 to 60 mm. Color: Yellow-Green Group 144B maturing to Greyed-Orange Group 177A. Clasping: By leaf petiole.

*Petioloule.*—Length: 2 to 10 mm. Color: Yellow-Green Group 144B.

*Leaflet shape.*—General shape: Elliptic. Base: Rounded. Apex: Acute.

*Margin.*—Entire.

*Leaflet size.*—30 to 60 mm in length by 20 to 30 mm wide.

*Texture.*—Smooth.

*Surface.*—Upper side: Glabrous. Lower side: Smooth.

*Thickness.*—Moderate.

*Glossiness.*—Matte Finish.

Disease resistance: Subject to any disease that normally attacks the species. However, the variety is more tolerant to *Botrytis* then some double forms of *Clematis.*

We claim:

1. A new and distinct variety of *Clematis* plant named 'Evipo011', described and illustrated herein as a distinct and novel *Clematis* variety due to its light purple flowers with distinct center, attractive long lasting foliage and compact growth, repeated flowering under glasshouse conditions, suitability for production from softwood cuttings in pots, durable flowers and foliage which make the variety suitable for distribution in the floral industry.

* * * * *

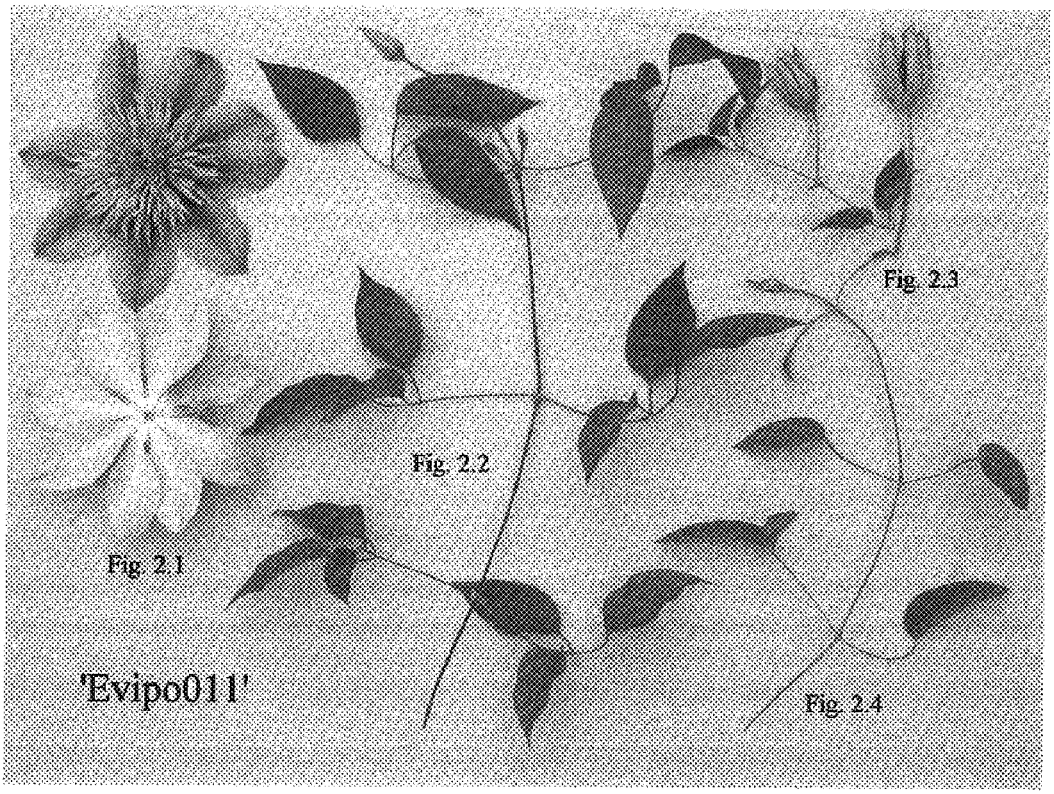
Fig. 2.3
Fig. 2.2
Fig. 2.1
'Evipo011'
Fig. 2.4